United States Patent [19]

Mederski et al.

[11] Patent Number: 5,332,750
[45] Date of Patent: Jul. 26, 1994

[54] 1,2-DIHYDRO-2-OXOPYRIDINES

[75] Inventors: Werner Mederski, Erzhausen; Norbert Beier, Reinheim; Pierre Schelling, Mühltal; Ingeborg Lues, Darmstadt; Klaus-Otto Minck, Ober-Ramstadt, all of Fed. Rep. of Germany

[73] Assignee: Merck Patent Gesellschaft mit beschrankter Haftung, Darmstadt, Fed. Rep. of Germany

[21] Appl. No.: 50,800

[22] Filed: Apr. 22, 1993

Related U.S. Application Data

[63] Continuation-in-part of Ser. No. 940,417, Sep. 3, 1992, abandoned.

[30] Foreign Application Priority Data

Sep. 4, 1991 [DE] Fed. Rep. of Germany ....... 4129340

[51] Int. Cl.$^5$ .................... A61K 31/44; C07D 401/04
[52] U.S. Cl. ....................................... 514/340; 546/276
[58] Field of Search ........................ 546/276; 514/340

[56] References Cited

U.S. PATENT DOCUMENTS

| | | | |
|---|---|---|---|
| 4,880,804 | 11/1989 | Carini et al. | 514/253 |
| 5,130,318 | 7/1992 | Roberts et al. | 514/299 |
| 5,236,936 | 8/1993 | Roberts et al. | 514/340 |
| 5,250,548 | 10/1993 | Winn et al. | 514/340 |

FOREIGN PATENT DOCUMENTS

| | | |
|---|---|---|
| 2051705 | 12/1991 | Canada . |
| 0400974 | 12/1990 | European Pat. Off. . |
| 0487745 | 6/1992 | European Pat. Off. . |
| 0500297 | 8/1992 | European Pat. Off. . |
| 91/19697 | 12/1991 | PCT Int'l Appl. . |

OTHER PUBLICATIONS

*Zeffren, *The Study of Enzyme Mechanism*, p. 87, 1974.
*Wade, Jr., *Organic Chemistry*, p. 349, 1987.
Aumailley et al., FEBS Letters, vol. 291, No. 1, pp. 50–54 (Oct. 1991).
Smith et al., The Journal of Biological Chemistry, vol. 265, No. 21, pp. 12267–12271 (Jul. 25, 1990).

*Primary Examiner*—Jane T. Fan
*Attorney, Agent, or Firm*—Millen, White, Zelano & Branigan

[57] ABSTRACT

New 1,2-dihydro-2-oxopyridines of formula I

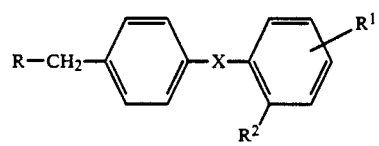

in which
R is the radical

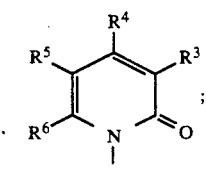

and
$R^1$ to $R^6$ and X are as defined herein, and their salts, have antagonistic properties towards angiotensin II and can be used for the treatment of hypertension, aldosteronism and cardiac insufficiency.

25 Claims, No Drawings

1,2-DIHYDRO-2-OXOPYRIDINES

This application is a continuation-in-part of application Ser. No. 07/940,417 filed Sep. 3, 1992, now abandoned herein incorporated by reference.

SUMMARY OF THE INVENTION

The invention relates to new 1,2-dihydro-2-oxopyridines of formula I

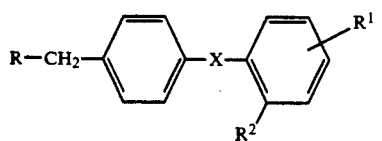

in which
R is the radical

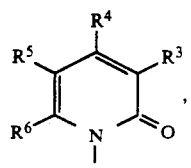

$R^1$ is H, Hal, A, OA or $NO_2$,
$R^2$ is COOH, COOA, CN, $NO_2$, $NH_2$, $NHCOR^7$, $NHSO_2R^7$ or tetrazol-5-yl,
$R^3$ is H, COOH, COOA, CHO, CN, $NO_2$, $CH_2R^8$, $CH_2OR^9$, $NR^{10}R^{11}$, $CH_2NR^{10}R^{11}$, $CONR^{10}R^{11}$ or tetrazol-5-yl,
$R^4$ is H or A,
$R^5$, $R^6$ and $R^{10}$ are in each case H, A, alkenyl having 2-6 C atoms, alkynyl having 2-6 C atoms, Ar or Ar-alkyl having 1-6 C atoms in the "alkyl" moiety,
$R^7$ is A or A monosubstituted or polysubstituted by F,
$R^8$ is H, Hal, A, Ar, CN, COOH, COOA, $CH_2COOH$, $CH_2COOA$ or tetrazol-5-yl,
$R^9$ is H, A, Ar, Ar—alkyl having 1-6 C atoms in the "alkyl" moiety, COA, COAr, COOA, COOAr, $CONR^{12}R^{13}$, COO—alkyl—Ar or A—O—alkyl having 1-6 C atoms in the "alkyl" moiety in each case,
$R^{11}$ is H, A, A monosubstituted or polysubstituted by F, Ar, Ar—alkyl having 1-6 C atoms in the "alkyl" moiety, CO—A, CO—Ar, CO—alkyl—Ar having 1-6 C atoms in the "alkyl" moiety, COOA, COOAr, COO—alkyl—Ar having 1-6 C atoms in the "alkyl" moiety, $CONR^{12}R^{13}$, $SO_2R^7$ or $SO_2Ar$, $NR^{10}R^{11}$ can also be pyrrolidino, piperidino, morpholino, succinimido or phthalimido,
$R^{12}$ and
$R^{13}$ are in each case H, A, cycloalkyl having 3-8 C atoms, alkenyl having 2-6 C atoms, alkynyl having 2-6 C atoms, or Ar,
X is absent or is —CO—, —O—, —NH—CO—, —CO—NH—, —$CH_2$—O— or —O—$CH_2$—,
A is alkyl having 1-6 C atoms,
is phenyl which is unsubstituted or monosubstituted by A, OA, $CF_3$, Hal or $NO_2$, and
Hal is F, Cl, Br or I,
wherein, however, at least one of the following provisos must be met:

(a) $R^1$ is Hal, A, OA or $NO_2$;
(b) $R^2$ is CN, $NO_2$, $NH_2$, $NHCOR^7$ or $NHSO_2R^7$;
(c) $R^3$ is $CH_2Ar$, $CH_2CN$, $CH_2COOH$, $CH_2COOA$, $CH_2CH_2COOH$, $CH_2CH_2COOA$, $CH_2$—(tetrazol-5-yl), $CH_2OAr$, $CH_2O$—alkyl—Ar'(wherein Ar' is a phenyl group monosubstituted by A, OA, $CF_3$, Hal or $NO_2$), $CH_2O$—CO—Ar', $CH_2OCOOAr$, $CH_2OCONR^{14}R^{15}$, (wherein $R^{14}$ and $R^{15}$, independently from each other, are alkenyl, alkynyl or Ar, one of $R^{14}$ and $R^{15}$ can also be H or A), $CH_2O$—COO—alkyl—Ar, $CH_2O$—alkyl—O—A, $NR^{16}R^{17}$ (wherein $R^{16}$ is alkenyl, alkynyl, Ar or Ar—alkyl, $R^{17}$ is A monosubstituted or polysubstituted by F, Ar, Ar—alkyl, CO—Ar, CO—alkyl—Ar, COOA, COOAr, COO—alkyl—Ar or $CONR^{12}R^{13}$, one of $R^{16}$ and $R^{17}$ can also be H or A), pyrrolidino, piperidino, morpholino, succinimido, phthalimido, $CH_2NR^{10}R^{11}$, or $CONR^{18}R^{19}$ (wherein $R^{18}$ is alkenyl, alkynyl, Ar or Ar—alkyl, $R^{19}$ is A monosubstituted or polysubstituted by F, Ar', Ar—alkyl, CO—Ar, CO—alkyl—Ar, COOA, COOAr, COO—alkyl—Ar or $CONR^{12}R^{13}$, one of $R^{18}$ and $R^{19}$ can also be H or A, the group $NR^{18}R^{19}$ can also be succinimido or phthalimido),
(d) $R^5$ is alkynyl, Ar' or Ar—alkyl;
(e) $R^6$ is alkynyl, Ar' or Ar—alkyl; or
(f) X is —CO—, —O—, —NH—CO—, —CO—NH—, —$CH_2$—O— or —O—$CH_2$—,
and their salts.

In the foregoing, selection of variables defined together is made independently.

Similar compounds are known from EP-A2-400974 and U.S. Pat. No. 4,880,804 and WO91/19697.

An object of the invention is to provide novel compounds with valuable properties, especially those which can be used for the preparation of drugs.

Upon further study of the specification and appended claims, further objects and advantages of this invention will become apparent to those skilled in the art.

It was found that the compounds of formula I and their salts possess very valuable pharmacological properties coupled with good tolerance. In particular, they have antagonistic properties towards angiotensin II and can therefore be used for the treatment of angiotensin II-dependent hypertension, aldosteronism and cardiac insufficiency. These effects can be determined by conventional in vitro or in vivo methods such as, for example, those described in U.S. Pat. No. 4,880,804 and also by A. T. Chiu et al., J. Pharmacol. Exp. Therap. 250, 867-874 (1989), and by P. C. Wong et al., ibid. 252, 719-725 (1990; in vivo, on rats).

The compounds of formula I can be used as pharmaceutical active ingredients in human and veterinary medicine, especially for the prophylaxis and/or therapy of cardiac, circulatory and vascular diseases, in particular of hypertonia, cardiac insufficiency and hyperaldosteronism.

The invention relates to the compounds of formula I and their salts and to a process for the preparation of these compounds and their salts, characterized in that (a) a compound of formula II:

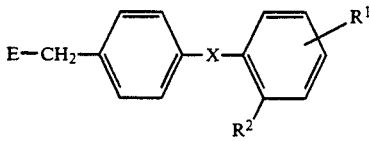

in which
E is Cl, Br, I, a free OH group or an OH group which has been functionally modified to acquire reactivity, and
$R^1$, $R^2$ and X are as defined above for formula I, is reacted with a compound of formula III:

H—R    III in which
R is as defined above for formula I,
or
(b) to prepare a compound of formula I in which X is —NH—CO— or —CO—NH—, a compound of formula IV:

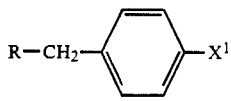

in which
$X^1$ is $NH_2$ or COOH and
R is as defined above for formula I,
or a reactive derivative of this compound, is reacted with a compound of formula V:

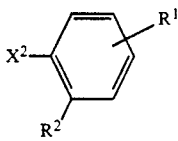

in which
$X^2$ is COOH (if $X^1$ is $NH_2$) or $NH_2$ (if $X^1$ is COOH) and
$R^1$ and $R^2$ are as defined above for formula I,
or with a reactive derivative of this compound, or (c) to prepare a compound of formula I in which X is —CH$_2$—O— or —O—CH$_2$—, a compound of formula VI:

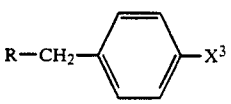

in which
$X^3$ is $CH_2E$ or OH and
R is as defined above for formula I,
or a reactive derivative of this compound, is reacted with a compound of formula VII:

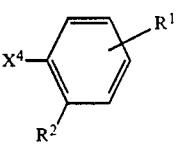

in which
$X^4$ is OH (if $X^3$ is $CH_2E$) or $CH_2E$ (if $X^3$ is OH) and
$R^1$ and $R^2$ are as defined above for formula I
or with a reactive derivative of this compound, or in that a compound of formula I is liberated from one of its functional derivatives by treatment with a solvolyzing or hydrogenolyzing agent, and/or in that one or more radicals $R^1$, $R^2$, $R^3$, $R^4$, $R^5$ and/or $R^6$ in a compound of formula I are converted to one or more other radicals $R^1$, $R^2$, $R^3$, $R^4$, $R^5$ and/or $R^6$, and/or a base or acid of formula I is converted to one of its salts.

Above and below, unless expressly indicated otherwise, the radicals or parameters R, $R^1$ to $R^{13}$, X, A, Ar, Hal, E, $X^1$, $X^2$, $X^3$ and $X^4$ are as defined in formulae I to VII.

In the above formulae, A has 1–6, preferably 1, 2, 3 or 4 C atoms. A is preferably methyl, ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3-or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl.

Typically, all "alkyl," "alkenyl" and "alkynyl" portions have up to 6 C atoms, including, for example, the alkylene portions of Ar-alkyl, CO-alkyl-Ar and COO-alkyl-Ar.

Ar is preferably unsubstituted phenyl, or else preferably o-, m- or p-tolyl, o-, m- or p-ethylphenyl, o-, m- or p-isopropylphenyl, o-, m- or p-methoxyphenyl, o-, m- or p-ethoxyphenyl, o-, m- or p-isopropoxyphenyl, o-, m- or p-trifluoromethylphenyl, o-, m- or p-fluorophenyl, o-, m- or p-chlorophenyl, o-, m- or p-bromophenyl or o-, m- or p-nitrophenyl.

Hal is preferably F, Cl or Br, or else I.

Alkenyl has 2–6, preferably 2, 3 or 4 C atoms and is preferably vinyl, allyl, prop-1-en-1-yl, prop-1-en-2-yl, but-1-, -2- or -3-en-1-yl or but-1-, -2- or -3-en-2-yl.

Alkynyl has 2–6, preferably 2, 3 or 4 C atoms and is preferably ethynyl, prop-1- or -3-yn-1-yl or but-1-, -2- or -3-yn-1-yl.

In Ar-alkyl the "alkyl" moiety has 1–6, preferably 1, 2 or 3 C atoms. Ar-alkyl is preferably benzyl, 1- or 2-phenylethyl or 1-, 2- or 3-phenylpropyl, or else preferably o-, m- or p-methylbenzyl, o, m- or p-methoxybenzyl, o-, m- or p-trifluoromethylbenzyl, o-, m-or p-fluorobenzyl, o-, m- or p-chlorobenzyl, o-, m- or p-bromobenzyl or o-, m- or p-nitrobenzyl.

"A substituted by F" is preferably $CH_2F$, $CHF_2$, $CF_3$, $CH_2$—$CF_3$, $CF_2$—$CF_3$, $CH_2$—$CH_2$—$CF_3$, $CH_2$—$CF_2$—$CF_3$, $C_3F_7$, $(CF_3)_2CH$ or iso—$C_3F_7$.

Cycloalkyl has 3–8, preferably 3, 4, 5 or 6 C atoms and is preferably cyclopropyl, cyclobutyl, cyclopentyl or cyclohexyl.

The radicals $R^1$, $R^4$ and $R^5$ are preferably H in each case, or else preferably A in each case.

The radical $R^3$ is preferably H, $CH_2OR^9$ (especially $CH_2OA$ such as methoxymethyl, ethoxymethyl, propoxymethyl, isopropoxymethyl, butoxymethyl, isobutoxymethyl, pentoxymethyl or hexyloxymethyl; or $CH_2O$-alkyl-Ar such as benzyloxymethyl), $CH_2NR^{10}R^{11}$ (especially $CH_2NHR^{11}$, in particular $CH_2NHA$ such as methylaminomethyl, ethylaminomethyl, propylaminomethyl, isopropylaminomethyl, butylaminomethyl, isobutylaminomethyl, pentylaminomethyl or hexylaminomethyl; $CH_2NH$-alkyl-Ar such as benzylaminomethyl; or $CH_2NA$—CO—NHAr such as N-methyl-N'- phenylureidomethyl, N-ethyl-N'-phenylureidomethyl, N-propyl-N'-phenylureidomethyl, N-isopropyl-N'-phenylureidomethyl, N-butyl-N'-phenylureidomethyl, N-isobutyl-N'-phenylureidomethyl, N-pentyl-N'-phenylureidomethyl or N-hexyl-N'-phenylureidomethyl) or tetrazol-5-yl. $R^3$ is also preferably COOA (especially methoxycarbonyl or ethoxycarbonyl), CHO, CN, $CH_2R^8$ (especially A such as methyl or ethyl) or $CONR^{10}R^{11}$ such as $CONH_2$.

Very particularly preferred radicals $R^3$ are H or tetrazol-5-yl, or else butoxymethyl, benzyloxymethyl, butylaminomethyl, benzylaminomethyl and N-butyl-N'-phenylureidomethyl.

The radical $R^6$ is preferably linear and is preferably A, alkenyl or alkynyl having 3-6 C atoms in each case, especially butyl, or else propyl, pentyl, hexyl, allyl or prop-1-enyl, or else but-1-enyl, pent-1-enyl, hex-1-enyl, prop-1-ynyl, but-1-ynyl, pent-1-ynyl or hex-1-ynyl.

The radical $R^7$ is preferably A, especially methyl or ethyl, or $CF_3$.

The radical $R^8$ is preferably H, F, Cl, A, CN, COOH, COOA or tetrazol-5-yl.

The radical $R^9$ is preferably H, A (especially having 3-5 C atoms) or benzyl.

The radical $R^{10}$ is preferably H, A or benzyl.

The radical $R^{11}$ is preferably H, A (especially having 1-5 C atoms), A polysubstituted by F, benzyl, CO—A, CO—Ar, CO—$CH_2C_6H_5$, COOA, COOAr, $COOCH_2C_6H_5$, $CONH_2$, CONHA, CONH-cycloalkyl, $CONA_2$ or CONHAr.

The radical X is preferably absent or is preferably —NH—CO— or —CO—NH—.

The compounds of formula I can possess one or more chiral centers and can therefore exist in different forms (optically active or optically inactive). Formula I includes all these forms.

Accordingly, the invention relates especially to those compounds of formula I in which at least one of said radicals has one of the preferred meanings indicated above. Some preferred groups of compounds can be expressed by the following partial formulae Ia to Ig, which correspond to formula I and in which the radicals not described more precisely are as defined in formula I, except that in Ia: $R^3$ is H;
in Ib: $R^3$ is COOH, COOA or $CONR^{10}R^{11}$;
in Ic: $R^3$ is CHO or CN;
in Id: $R^3$ is $CH_2R^8$;
in Ie: $R^3$ is $CH_2OR^8$;
in If: $R^3$ is $NR^{10}R^{11}$ or $CH_2NR^{10}R^{11}$; and
in Ig: $R^3$ is tetrazol-5-yl.

Particularly preferred compounds are those of formulae Ih and Iah to Igh, which correspond to formulae I and Ia to Ig except that in addition X is absent.

Other preferred compounds are those of formulae Ii and Iai to Igi, which correspond to formulae I and Ia to Ig except that in addition X is —CO—.

Other preferred compounds are those of formulae Ij and Iaj to Igj, which correspond to formulae I and Ia to Ig except that in addition X is —O—.

Other preferred compounds are those of formulae Ik and Iak to Igk, which correspond to formulae I and Ia to Ig except that in addition X is —NH—CO—.

Other preferred compounds are those of formulae Il and Ial to Igl, which correspond to formulae I and Ia to Ig except that in addition X is —CO—NH—.

Other preferred compounds are those of formulae Im and Iam to Igm, which correspond to formulae I and Ia to Ig except that in addition X is —$CH_2$—O—.

Other preferred compounds are those of formulae In and Ian to Ign, which correspond to formulae I and Ia to Ig except that in addition X is —O—$CH_2$—.

Particularly preferred compounds are those of formulae I, Ia to In and Iah to Ign in which in addition $R^1$ is H and/or $R^4$ are H or A and/or $R^6$ is A (especially propyl, butyl or pentyl).

Among these, preferred compounds are those in which $R^2$ is COOH, $COOCH_3$, $COOC_2H_5$, CN or tetrazol-5-yl.

A very particularly preferred group of compounds is that of formula I in which $R^1$ is H,
$R^2$ is COOH, COOA, CN or tetrazol-5-yl,
$R^3$ is H, $CH_2OA$, $CH_2OCH_2C_6H_5$, $CH_2NHA$, $CH_2NHCH_2C_6H_5$, $CH_2NACONHC_6H_5$ or tetrazol-5-yl,
$R^4$ and $R^5$ are H or A in each case,
$R^6$ is A and
X is absent.

A small selected group of preferred compounds is that of formula I in which $R^1$, $R^4$ and $R^5$ are H in each case,
$R^2$ is CN or tetrazol-5-yl,
$R^3$ is H, $CH_2O$-alkyl having 3-5 C atoms in the alkyl group, or tetrazol-5-yl,
$R^6$ is alkyl having 3-5 C atoms and
X is absent.

The compounds of formula I and also the starting materials for their preparation are moreover prepared by methods known per se, such as those described in the literature (for example in the standard works like Houben-Weyl, Methoden der organischen Chemie (Methods of Organic Chemistry), Georg-Thieme-Verlag, Stuttgart, but especially U.S. Pat. No. 4,880,804), under reaction conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of formula I.

The compounds of formula I can preferably be obtained by reacting compounds of formula II with compounds of formula III. Particularly the biphenyl derivatives of formula I (in which X is absent) are readily obtainable in this way.

In the compounds of formula II, E is preferably Cl, Br, I or an OH group which has been functionally modified to acquire reactivity, such as alkylsulfonyloxy having 1-6 C atoms (preferably methylsulfonyloxy) or arylsulfonyloxy having 6-10 C atoms (preferably phenyl-or p-tolyl-sulfonyloxy).

The reaction of II with III is conveniently carried out by first converting III to a salt by treatment with a base, for example with an alkali metal alcoholate such as $CH_3ONa$ in an alcohol such as $CH_3OH$, or with NaH or potassium tert-butylate in dimethylformamide (DMF), and then reacting said salt with II in an inert solvent, for example an amide such as DMF or dimethylacetamide, or a sulfoxide such as dimethyl sulfoxide (DMSO), conveniently at temperatures of between −20° and 100°, preferably of between 10° and 30°.

Acid amides of formula I (X=—NH—CO— or —CO—NH—) can also be obtained by reacting compounds of formula IV (or reactive derivatives thereof) with compounds of formula V (or reactive derivatives thereof). Suitable reactive derivatives of the carboxylic acids of formulae IV and V ($X^1$ or $X^2$=COOH) are advantageously the corresponding chlorides, bromides or anhydrides. The reaction is conveniently carried out in the presence of an inert solvent, for example a halogenated hydrocarbon such as methylene chloride, chloroform, trichloroethene or 1,2-dichloroethane, or an ether such as tetrahydrofuran (THF) or dioxane, at temperatures of between 0° and 150°, preferably of between 20° and 80°. If acid halides are reacted, it is recommended to add a base, for example a tertiary amine such as triethylamine, pyridine or 4-dimethylaminopyridine.

Ethers of formula I (X=—CH$_2$—O—or —O—CH$_2$—) can be obtained by reacting compounds of formulae VI and VII (or reactive derivatives thereof). Examples of suitable reactive derivatives of the phenols VI and VII ($X^3$ or $X^4$=OH) are the corresponding alkali metal (for example Na, K) phenolates, which can also be formed in situ from the phenol and a base (for example potassium carbonate). The reaction is conveniently carried out in the presence of an inert solvent, for example an amide such as DMF or a sulfoxide such as DMSO, at temperatures of between 0° and 150°, preferably of between 20° and 100°.

Some of the starting materials of formulae II, III, IV, V, VI and VII are known. If they are not known, they can be prepared by known methods analogously to known substances. Compounds of formula II are extensively known (compare, for example, EP-A2-400974). Compounds of formula III can be obtained for example by reacting ketones of the formula $R^6$—CO—CH$_2$—$R^5$ (preferably $R^6$—CO—CH$_3$) with esters of the formula $R^4$—COOA (preferably HCOOA, especially HCOOC$_2$H$_5$) to give dicarbonyl compounds of the formula $R^6$—CO—C$R^5$=C$R^4$—OH (preferably $R^6$—CO—CH=CH—OH; "enolone form") and then condensing these with acetamides of the formula $R^3$—CH$_2$—CONH$_2$, especially cyanoacetamide. It is thus possible in particular to obtain 3-cyano-4-$R^4$-5-$R^5$-6-$R^6$-1,2-dihydro-2-oxopyridines (formula III, $R^3$=CN, $R^4$=$R^5$=H), for example 6-butyl-3-cyano-1,2-dihydro-2-oxopyridine ("IIIb"). The following are examples of compounds which can be obtained from these 3-cyano compounds: by hydrolysis (for example with hydrochloric acid), the carboxylic acids (III, $R^3$=COOH); from these, by esterification (for example with an alcohol A—OH in the presence of a strong acid), the esters (III, $R^3$ = COOA); by decarboxylation, the 1,2-dihydro-2-oxopyridines unsubstituted in the 3-position (III, $R^3$=H); by reduction, the 3-hydroxymethyl compounds (III, $R^3$=CH$_2$OH) or the 3-aminomethyl compounds (III, $R^3$=CH$_2$NH$_2$); and by oxidation of the latter, for example with MnO$_2$, the aldehydes (III, $R^3$=CHO), which can also be prepared from the nitriles by reaction with diisobutylaluminium hydride. Partial hydrolysis of the nitriles (III, $R^3$=CN; for example with 90% H$_2$SO$_4$; compare U.S. Pat. No. 4,137,233) gives the carboxamides (III, $R^3$=CONH$_2$), which can be degraded with NaOH/Br$_2$ to the 3-amino compounds (III, $R^3$=NH$_2$) (compare U.S. Pat. No. 4,137,233).

To convert a radical $R^3$ in starting materials of formula III, it is also possible to block the 2-oxo group as an intermediate step. Thus, for example, nitriles (III, $R^3$=CN) can be converted to the corresponding 2-benzyloxy-3-cyano-4-$R^4$-5-$R^5$-6-$R^6$-pyridines with benzyl chloride/Ag$_2$O in boiling toluene; the corresponding 3-carboxylic acids can be obtained from these by boiling with ethanolic KOH and the corresponding 3-hydroxymethyl compounds can be obtained by reducing said acids. Alkylation, for example with iodides of the formula A-I, gives the corresponding 2-benzyloxy-3-alkoxymethyl-4-$R^4$-5-$R^5$-6-$R^6$-pyridines, which can be hydrogenolyzed to compounds of formula III ($R^3$=A—O—CH$_2$).

A compound of formula I can also be liberated from one of its functional derivatives by treatment with a solvolyzing (for example hydrolyzing) or hydrogenolyzing agent.

It is thus possible, using one of the indicated methods, to prepare a compound which has formula I but in which the tetrazol-5-yl group is replaced with a tetrazol-5-yl group functionally modified in the 1-position (protected by a protecting group). Examples of suitable protecting groups are: triphenylmethyl, which can be cleaved with HCl in an inert solvent or solvent mixture, for example ether/methylene chloride/methanol; 2-cyanoethyl, which can be cleaved with NaOH in water/THF; and p-nitrobenzyl, which can be cleaved with H$_2$/Raney nickel in ethanol (compare EP-A2-0 291 969).

It is also possible to convert one compound of formula I to another compound of formula I by converting one or more of the radicals $R^1$, $R^2$, $R^3$, $R^4$, $R^5$ and/or $R^6$ to other radicals $R^1$, $R^2$, $R^3$, $R^4$, $R^5$ and/or $R^6$, for example by reducing nitro groups to amino groups (for example by hydrogenation on Raney nickel in an inert solvent such as methanol or ethanol), and/or functionally modifying free amino and/or hydroxyl groups, and/or liberating functionally modified amino and/or hydroxyl groups by solvolysis or hydrogenolysis, and/or replacing halogen atoms with OA or CN groups (for example by reaction with alkali metal alcoholates or with copper(I) cyanide), and/or hydrolyzing nitrile groups to CONH$_2$ or COOH groups, or converting nitrile groups to tetrazolyl groups with hydrazoic acid derivatives, and/or reducing CHO groups to CH$_2$OH groups (for example with NaBH$_4$), or converting CHO groups to aminomethyl, A—NH—CH$_2$ or Ar-alkyl-NH—CH$_2$ groups (for example with ammonia or primary amines in the presence of a reducing agent such as NaCNBH$_3$), and/or degrading CONH$_2$ groups to NH$_2$ groups (for example with Br$_2$/aqueous NaOH solution).

Thus, for example, free hydroxyl and/or amino groups can be acylated in a conventional manner with an acid chloride or anhydride, or alkylated with an alkyl or aralkyl chloride or bromide, conveniently in an inert solvent such as methylene chloride or THF, and/or in the presence of a base such as triethylamine or pyridine, at temperatures of between −60° and +30°. The conversion of primary amino groups to secondary or tertiary amino groups is also effected by reaction with appropriate aldehydes or ketones in the presence of a reducing agent.

If desired, a functionally modified amino and/or hydroxyl group in a compound of formula I can be liberated by solvolysis or hydrogenolysis using conventional methods. Thus, for example, a compound of formula I containing an NHCOR$^7$, NHCOOA or AOOC group can be converted to the corresponding compound of formula I containing an NH$_2$ or HOOC group instead. AOOC groups can be saponified for example with NaOH or KOH in water, water/THF or water/dioxane at temperatures of between 0° and 100°.

The reaction of nitriles of formula I ($R^2$ and/or $R^3$=CN) with hydrazoic acid derivatives gives tetrazoles of formula I ($R^2$ and/or $R^3$=tetrazol-5-yl). It is preferable to use trialkyltin azides such as trimethyltin azide, in an inert solvent, for example an aromatic hydrocarbon such as toluene, at temperatures of between 20° and 150°, preferably of between 80° and 140°, or sodium azide in N-methylpyrrolidone at temperatures of between about 100° and 200°.

A base of formula I can be converted with an acid to the corresponding acid addition salt. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphoric acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example picrates, can be used for isolating and/or purifying the compounds of formula I.

On the other hand, compounds of formula I containing COOH or tetrazolyl groups can be converted with bases (for example sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of formula I and their physiologically acceptable salts can be used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; film-coated tablets and capsules with coatings or shells resistant to gastric juice are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant mixture (for example chlorofluorocarbons). It is convenient here to use the active ingredient in micronized form, it being possible for one or more additional physiologically compatible solvents, for example ethanol, to be present. Inhalation solutions can be administered with the aid of conventional inhalers. The novel compounds can also be lyophilized and the resulting lyophilizates used for example for the manufacture of injectable preparations. The indicated formulations can be sterilized and/or can contain adjuncts such as preservatives, stabilizers and/or wetting agents, emulsifiers, salts for influencing the osmotic pressure, buffer substances and colorants and/or flavorings. If desired, they can also contain one or more other active ingredients, for example one or more vitamins, diuretics or antiphlogistics.

The substances according to the invention are normally administered analogously to other known, commercially available preparations, but in particular analogously to the compounds described in U.S. Pat. No. 4,880,804, preferably in doses of about 1 mg-1 g, especially 50-500 mg per dosage unit. The daily dose is preferably about 0.1-50 mg/kg, especially 1-10 mg/kg of body weight. However, the particular dose for each individual patient depends on a very wide variety of factors, for example on the efficacy of the particular compound used, age, body weight, general state of health, sex, diet, time and method of administration, rate of excretion, drug combination and severity of the particular disease to which the therapy is applied. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above, and of corresponding German application P 41 29 340.1, are hereby incorporated by reference.

In the examples which follow, "conventional working-up" means water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization.

$M^+$ =molecular peak in the mass spectrum. Rf values by thin layer chromatography on silica gel with methylene chloride/methanol (99:1 unless indicated otherwise).

EXAMPLE 1

1.12 g of potassium tert-butylate are added to a solution of 1.5 g of 6-butyl-1,2-dihydro-2-oxopyridine ["IIIa"; m.p. 69°; obtainable by condensation of hexan-2-one with ethyl formate in toluene, in the presence of NaOCH$_3$, to give 1-hydroxyhept-1-en-3-one, condensation with cyanoacetamide in water, in the presence of piperidine and acetic acid, at 90°, to give 6-butyl-3-cyano-1,2-dihydro-2-oxopyridine ("IIIb"; m.p. 110°), hydrolysis with 37% hydrochloric acid (boiling for 5 hours) to give 6-butyl-1,2-dihydro-2-oxopyridine-3-carboxylic acid (m.p. 149°) and decarboxylation at 180°–200°] in 25 ml of DMF. The mixture is stirred for 10 minutes, a solution of 2.72 g of 4'-bromomethyl-2-cyanobiphenyl ("IIa") in 15 ml of DMF is added dropwise over 30 minutes and the resulting mixture is stirred for 16 hours at 20°. It is evaporated, worked up in a conventional manner (pH 7; ethyl acetate) and purified by chromatography (silica gel; methylene chloride/methanol 98:2) to give 6-butyl-1-(2'-cyanobiphenyl-4-ylmethyl)-1,2-dihydro-2-oxopyridine; Rf 0.4; (M+H)+ 343. 6-Butyl-2-(2'-cyanobiphenyl-4-yl-methoxy)pyridine is obtained as a by-product.

The following are obtained analogously from IIIa:
with 4-bromomethyl-2'-methoxycarbonylbenzanilide (m.p. 151°; obtainable from 4-methyl-2'-methoxycarbonylbenzanilide and N-bromosuccinimide in methylene chloride):
6-butyl-1-[4-(2-methoxycarbonylanilinocarbonyl)benzyl]-1,2-dihydro-2-oxopyridine;
with 4-bromomethyl-2'-nitrobiphenyl:
6-butyl-1-(2'-nitrobiphenyl-4-ylmethyl)-1,2-dihydro-2-oxopyridine;
with 4-bromomethyl-2'-methoxycarbonylbenzophenone:
6-butyl-1-[4-(2-methoxycarbonylbenzoyl)benzyl]-1,2-dihydro-2-oxopyridine;
with 4-(2-cyanobenzamido)benzyl bromide:
6-butyl-1-[4-(2-cyanobenzamido)benzyl]-1,2-dihydro-2-oxopyridine;
with 4-(2-cyanoanilinocarbonyl)benzyl bromide:
6-butyl-1-[4-(2-cyanoanilinocarbonyl)benzyl]-1,2-dihydro-2-oxopyridine.

EXAMPLE 2

The following are obtained from IIa analogously to Example 1:
with methyl 6-butyl-1,2-dihydro-2-oxopyridine-3-carboxylate [m.p. 126°; obtainable by esterification of the carboxylic acid (m.p. 149°; see Example 1)]:
methyl 6-butyl-1-(2'-cyanobiphenyl-4-ylmethyl)-1,2-dihydro-2-oxopyridine-3-carboxylate, m.p. 142°;
with 6-butyl-3-carbamoyl-1,2-dihydro-2-oxopyridine (m.p. 205°; obtainable from IIIb and 90% $H_2SO_4$):
6-butyl-3-carbamoyl-1-(2'-cyanobiphenyl-4-ylmethyl)-1,2-dihydro-2-oxopyridine;
with 6-butyl-1,2-dihydro-2-oxo-3-formylpyridine (m.p. 118°; obtainable from IIIb with diisobutylaluminium hydride in toluene at −65°):
6-butyl-1-(2'-cyanobiphenyl-4-ylmethyl)-1,2-dihydro-2-oxo-3-formylpyridine;
with IIIb:
6-butyl-1-(2'-cyanobiphenyl-4-ylmethyl)-1,2-dihydro-2-oxo-3-cyanopyridine; Rf 0.25;
with 6-butyl-1,2-dihydro-2-oxo-3-nitropyridine:
6-butyl-1-(2'-cyanobiphenyl-4-ylmethyl)-1,2-dihydro-2-oxo-3-nitropyridine;
with 6-butyl-1,2-dihydro-2-oxo-3-dimethylaminocarbonylpyridine:
6-butyl-1-(2'-cyanobiphenyl-4-ylmethyl)-1,2-dihydro-2-oxo-3-dimethylaminocarbonylpyridine;
with 6-butyl-1,2-dihydro-2-oxo-3-pyrrolidinopyridine:
6-butyl-1-(2'-cyanobiphenyl-4-ylmethyl)-1,2-dihydro-2-oxo-3-pyrrolidinopyridine;
with 6-butyl-1,2-dihydro-2-oxo-3-piperidinopyridine:
6-butyl-1-(2'-cyanobiphenyl-4-ylmethyl)-1,2-dihydro-2-oxo-3-piperidinopyridine;
with 6-butyl-1,2-dihydro-2-oxo-3-succinimidopyridine:
6-butyl-1-(2'-cyanobiphenyl-4-ylmethyl)-1,2-dihydro-2-oxo-3-succinimidopyridine;
with 6-butyl-1,2-dihydro-2-oxo-3-phthalimidopyridine:
6-butyl-1-(2'-cyanobiphenyl-4-ylmethyl)-1,2-dihydro-2-oxo-3-phthalimidopyridine;
with 6-butyl-1,2-dihydro-2-oxo-3-acetamidopyridine:
6-butyl-1-(2'-cyanobiphenyl-4-ylmethyl)-1,2-dihydro-2-oxo-3-acetamidopyridine;
with 6-butyl-1,2-dihydro-2-oxo-3-trimethylacetamidopyridine:
6-butyl-1-(2'-cyanobiphenyl-4-ylmethyl)-1,2-dihydro-2-oxo-3-trimethylacetamidopyridine;
with 6-butyl-1,2-dihydro-2-oxo-3-benzamidopyridine:
6-butyl-1-(2'-cyanobiphenyl-4-ylmethyl)-1,2-dihydro-2-oxo-3-benzamidopyridine;
with 6-butyl-1,2-dihydro-2-oxo-3-tert-butoxycarbonylaminopyridine:
6-butyl-1-(2'-cyanobiphenyl-4-ylmethyl)-1,2-dihydro-2-oxo-3-tert-butoxycarbonylaminopyridine;
with 6-butyl-1,2-dihydro-2-oxo-3-N'-butylureidopyridine:
6-butyl-1-(2'-cyanobiphenyl-4-ylmethyl)-1,2-dihydro-2-oxo-3-N'-butylureidopyridine;
with 6-butyl-1,2-dihydro-2-oxo-3-N'-phenylureidopyridine:
6-butyl-1-(2'-cyanobiphenyl-4-ylmethyl)-1,2-dihydro-2-oxo-3-N'-phenylureidopyridine;
with 6-butyl-1,2-dihydro-2-oxo-3-N'-benzylureidopyridine:
6-butyl-1-(2'-cyanobiphenyl-4-ylmethyl)-1,2-dihydro-2-oxo-3-N'-benzylureidopyridine;
with 6-butyl-1,2-dihydro-2-oxo-3-N-methylbenzamidopyridine:
6-butyl-1-(2'-cyanobiphenyl-4-ylmethyl)-1,2-dihydro-2-oxo-3-N-methylbenzamidopyridine;
with 6-butyl-1,2-dihydro-2-oxo-3-methylpyridine (obtainable by hydrogenolysis of 3-acetoxymethyl-2-benzyloxy-6-butylpyridine on Pd/C in ethanol at 20° and 1 bar):
6-butyl-1-(2'-cyanobiphenyl-4-ylmethyl)-1,2-dihydro-2-oxo-3-methylpyridine; m.p. 126°; Rf 0.4;
with 6-butyl-1,2-dihydro-2-oxo-3-fluoromethylpyridine:
6-butyl-1-(2'-cyanobiphenyl-4-ylmethyl)-1,2-dihydro-2-oxo-3-fluoromethylpyridine;
with 6-butyl-1,2-dihydro-2-oxo-3-chloromethylpyridine:
6-butyl-1-(2'-cyanobiphenyl-4-ylmethyl)-1,2-dihydro-2-oxo-3-chloromethylpyridine;
with 6-butyl-1,2-dihydro-2-oxo-3-cyanomethylpyridine:
6-butyl-1-(2'-cyanobiphenyl-4-ylmethyl)-1,2-dihydro-2-oxo-3-cyanomethylpyridine;
with ethyl 6-butyl-1,2-dihydro-2-oxopyridine-3-acetate:
ethyl 6-butyl-1-(2'-cyanobiphenyl-4-ylmethyl)-1,2-dihydro-2-oxopyridine-3-acetate;
with 6-butyl-1,2-dihydro-2-oxo-3-methoxymethylpyridine:
6-butyl-1-(2'-cyanobiphenyl-4-ylmethyl)-1,2-dihydro-2-oxo-3-methoxymethylpyridine;
with 6-butyl-1,2-dihydro-2-oxo-3-isopropoxymethylpyridine:
6-butyl-1-(2'-cyanobiphenyl-4-ylmethyl)-1,2-dihydro-2-oxo-3-isopropoxymethylpyridine;
with 6-butyl-1,2-dihydro-2-oxo-3-butoxymethylpyridine [oil; obtainable by reaction of IIIb with benzyl chloride in the presence of $Ag_2O$ in toluene (boiling for 24 hours) to give 2-benzyloxy-6-butyl-3-cyanopyridine (oil), hydrolysis with aqueous-ethanolic KOH (boiling for 48 hours) to give 2-benzyloxy-6-butylnicotinic acid, reduction with LiAlH₄ in THF to give 2-benzyloxy-6-butyl-3-hydroxymethylpyridine, alkylation with butyl iodide in THF in the presence of NaH to give 2-benzyloxy-6-butyl-3-butoxymethylpyridine, and hydrogenolysis on 5% Pd/C in methanol]:
6-butyl-1-(2'-cyanobiphenyl-4-ylmethyl)-1,2-dihydro-2-oxo-3-butoxymethylpyridine; Rf 0.2;
with 6-butyl-1,2-dihydro-2-oxo-3-benzyloxymethylpyridine:
6-butyl-1-(2'-cyanobiphenyl-4-ylmethyl)-1,2-dihydro-2-oxo-3-benzyloxymethylpyridine, m.p. 150°;
with 6-butyl-1,2-dihydro-2-oxo-3-acetamidomethylpyridine:
6-butyl-1-(2'-cyanobiphenyl-4-ylmethyl)-1,2-dihydro-2-oxo-3-acetamidomethylpyridine;
with 6-butyl-1,2-dihydro-2-oxo-3-butyramidomethylpyridine:
6-butyl-1-(2'-cyanobiphenyl-4-ylmethyl)-1,2-dihydro-2-oxo-3-butyramidomethylpyridine;
with 6-butyl-1,2-dihydro-2-oxo-3-phenylacetamidomethylpyridine:
6-butyl-1-(2'-cyanobiphenyl-4-ylmethyl)-1,2-dihydro-2-oxo-3-phenylacetamidomethylpyridine;
with 6-butyl-1,2-dihydro-2-oxo-3-tert-butoxycarbonylaminomethylpyridine:
6-butyl-1-(2'-cyanobiphenyl-4-ylmethyl)-1,2-dihydro-2-oxo-3-tert-butoxycarbonylaminomethyl pyridine, m.p. 105°;
with 6-butyl-1,2-dihydro-2-oxo-3-phenoxycarbonylaminomethylpyridine:
6-butyl-1-(2'-cyanobiphenyl-4-ylmethyl)-1,2-dihydro-2-oxo-3-phenoxycarbonylaminomethylpyridine;
with 6-butyl-1,2-dihydro-2-oxo-3-benzyloxycarbonylaminomethylpyridine:
6-butyl-1-(2'-cyanobiphenyl-4-ylmethyl)-1,2-dihydro-2-oxo-3-benzyloxycarbonylaminomethylpyridine, oil, Rf 0.58 (ethylacetate/hexane 1:1)
with 6-butyl-1,2-dihydro-2-oxo-3-ureidomethylpyridine:
6-butyl-1-(2'-cyanobiphenyl-4-ylmethyl)-1,2-dihydro-2-oxo-3-ureidomethylpyridine, m.p. 166°;
with 6-butyl-1,2-dihydro-2-oxo-3-(N'-butylureidomethyl)pyridine:
6-butyl-1-(2'-cyanobiphenyl-4-ylmethyl)-1,2-dihydro-2-oxo-3-(N'-butylureidomethyl)pyridine, m.p. 61°;
with 6-butyl-1,2-dihydro-2-oxo-3-(N'-cyclohexylureidomethyl)pyridine:
6-butyl-1-(2'-cyanobiphenyl-4-ylmethyl)-1,2-dihydro-2-oxo-3-(N'-cyclohexylureidomethyl)pyridine, m.p. 98°;
with 6-butyl-1,2-dihydro-2-oxo-3-(N'-phenylureidomethyl)pyridine:
6-butyl-1-(2'-cyanobiphenyl-4-ylmethyl)-1,2-dihydro-2-oxo-3-(N'-phenylureidomethyl)pyridine, m.p. 89°;
with 6-butyl-1,2-dihydro-2-oxo-3-(N',N'-dimethylureidomethyl)pyridine:
6-butyl-1-(2'-cyanobiphenyl-4-ylmethyl)-1,2-dihydro-2-oxo-3-(N',N'-dimethylureidomethyl)pyridine, m.p. 60°;
with 6-butyl-1,2-dihydro-2-oxo-3-diethylaminomethylpyridine:
6-butyl-1-(2'-cyanobiphenyl-4-ylmethyl)-1,2-dihydro-2-oxo-3-diethylaminomethylpyridine;
with 6-butyl-1,2-dihydro-2-oxo-3-diisopropylaminomethylpyridine:
6-butyl-1-(2'-cyanobiphenyl-4-ylmethyl)-1,2-dihydro-2-oxo-3-diisopropylaminomethylpyridine;
with 6-butyl-1,2-dihydro-2-oxo-3-pyrrolidinomethylpyridine:
6-butyl-1-(2'-cyanobiphenyl-4-ylmethyl)-1,2-dihydro-2-oxo-3-pyrrolidinomethylpyridine;
with 6-butyl-1,2-dihydro-2-oxo-3-piperidinomethylpyridine:
6-butyl-1-(2'-cyanobiphenyl-4-ylmethyl)-1,2-dihydro-2-oxo-3-piperidinomethylpyridine;
with 6-butyl-1,2-dihydro-2-oxo-3-(N-methylacetamidomethyl)pyridine:
6-butyl-1-(2'-cyanobiphenyl-4-ylmethyl)-1,2-dihydro-2-oxo-3-(N-methylacetamidomethyl)pyridine;
with 6-butyl-1,2-dihydro-2-oxo-3-(N-isopropylacetamidomethyl)pyridine:
6-butyl-1-(2'-cyanobiphenyl-4-ylmethyl)-1,2-dihydro-2-oxo-3-(N-isopropylacetamidomethyl)pyridine;
with 6-butyl-1,2-dihydro-2-oxo-3-(N-butyl-N'-methylureidomethyl)pyridine:
6-butyl-1-(2'-cyanobiphenyl-4-ylmethyl)-1,2-dihydro-2-oxo-3-(N-butyl-N'-methylureidomethyl)pyridine;
with 6-butyl-1,2-dihydro-2-oxo-3-(N,N'-dimethylureidomethyl)pyridine:
6-butyl-1-(2'-cyanobiphenyl-4-ylmethyl)-1,2-dihydro-2-oxo-3-(N,N'-dimethylureidomethyl)pyridine;
with 6-butyl-1,2-dihydro-2-oxo-3-(N,N',N'-trimethylureidomethyl)pyridine:
6-butyl-1-(2'-cyanobiphenyl-4-ylmethyl)-1,2-dihydro-2-oxo-3-(N,N',N'-trimethylureidomethyl)pyridine;
with 6-butyl-1,2-dihydro-2-oxo-3-(N-butyl-N'-phenylureidomethyl)pyridine:
6-butyl-1-(2'-cyanobiphenyl-4-ylmethyl)-1,2-dihydro-2-oxo-3-(N-butyl-N'-phenylureidomethyl)pyridine;
with 6-butyl-1,2-dihydro-2-oxo-3-(N-benzyl-N'-methylureidomethyl)pyridine:
6-butyl-1-(2'-cyanobiphenyl-4-ylmethyl)-1,2-dihydro-2-oxo-3-(N-benzyl-N'-methylureidomethyl)pyridine;
with 6-butyl-1,2-dihydro-2-oxo-3-(N-butyl-N-isobutoxycarbonylaminomethyl)pyridine:
6-butyl-1-(2'-cyanobiphenyl-4-ylmethyl)-1,2-dihydro-2-oxo-3-(N-butyl-N-isobutoxycarbonylaminomethyl)pyridine;
with 6-butyl-1,2-dihydro-2-oxo-3-(N-isopropyl-N-benzyloxycarbonylaminomethyl)pyridine:
6-butyl-1-(2'-cyanobiphenyl-4-ylmethyl)-1,2-dihydro-2-oxo-3-(N-isopropyl-N-benzyloxycarbonylaminomethyl)pyridine;
with 4-methyl-1,2-dihydro-2-oxopyridine:
4-methyl-1,2-dihydro-2-oxo-1-(2'-cyanobiphenyl-4-ylmethyl)pyridine; Rf 0.1;
with 1,2-dihydro-2-oxo-6-phenylpyridine:
1-(2'-cyanobiphenyl-4-ylmethyl)-1,2-dihydro-2-oxo-6-phenylpyridine; Rf 0.5;
with methyl 6-isobutyl-1,2-dihydro-2-oxopyridine-3-carboxylate (obtainable analogously to IIIa from 4-methylpentan-2-one via 1-hydroxy-5-methylhexen-1-one, 6-isobutyl-1,2-dihydro-2-oxo-3-cyanopyridine and 6-isobutyl-1,2-dihydro-2-oxopyridine-3-carboxylic acid):
methyl 1-(2'-cyanobiphenyl-4-ylmethyl)-6-isobutyl-1,2-dihydro-2-oxopyridine-3-carboxylate; Rf 0.5;
with 3-cyano-6-methyl-1,2-dihydro-2-oxo-5-propylpyridine (formed as a by-product in the preparation of IIIb):
3-cyano-1-(2'-cyanobiphenyl-4-methyl)-6-methyl-1,2-dihydro-2-oxo-5-propylpyridine; m.p. 186°;
with 6-methyl-, 6-ethyl-, 6-propyl- or 6-pentyl-1,2-dihydro-2-oxopyridine:

1-(2'-cyanobiphenyl-4-ylmethyl)-6-methyl-1,2-dihydro-2-oxopyridine;
1-(2'-cyanobiphenyl-4-ylmethyl)-6-ethyl-1,2-dihydro-2-oxopyridine;
1-(2'-cyanobiphenyl-4-ylmethyl)-6-propyl-1,2-dihydro-2-oxopyridine;
1-(2'-cyanobiphenyl-4-ylmethyl)-6-pentyl-1,2-dihydro-2-oxopyridine.

EXAMPLE 3 a) A solution of 2.8 g of 3-tert.-butoxycarbonylaminomethyl-6-butyl-1,2-dihydro-2-oxo-pyridine [m.p. 147°; obtainable by hydrogenation of 6-butyl-3-cyano-1,2-dihydro-2-oxo-pyridine with Raney-nickel in ethanol in presence of $NH_3$ at 5 bar to yield 3-aminomethyl-6-butyl-1,2-dihydro-2-oxopyridine (m.p. 83°) and reaction with 2,2,8,8-tetramethyl-3,5,7-trioxa-4,6-dioxo-nonane in THF] in 35 ml of DMF is treated, with stirring, with 1.1 g of potassium tert.butylate and then, after ½ hour, with 5.45 g of 4'-bromomethyl-2-[1(or 2)-triphenylmethyl-1H(or 2H)tetrazol-5-yl]biphenyl (compare European patent application A2-0 392 317, where it is called "1-triphenylmethyl-1H", although without proof of structure) and the mixture is stirred for 3 hours at 20°. 3-tert.-Butoxycarbonylaminomethyl-6-butyl-1,2-dihydro-2-oxo-1-[2'-(1-triphenylmethyl-1H-tetrazol-5-yl)biphenyl-4-ylmethyl]-pyridine is obtained after conventional working-up (ethyl acetate).

b) A solution of 7.45 g of the product obtained according to a) in 20 ml of methylene chloride and 20 ml of methanol is treated with 20 ml of ethereal hydrochlorid acid and the mixture is stirred for 3 hours at 20°. It is evaporated and worked up in conventional manner to give 3-tert.-Butoxy-carbonyl-aminomethyl-6-butyl-1,2-dihydro-2-oxo-1-[2'-(tetrazol-5-yl)-biphenyl-4-ylmethyl]pyridine, m.p. 112°, after chromatrographic separation of the triphenylcarbinol formed.

The following 6-butyl-1,2-dihydro-2-oxo-1-[2'(tetrazol-5-yl)biphenyl-4-ylmethyl]pyridines are obtained analogously with the 6-butyl-1,2-dihydro-2-oxopyridines indicated in Example 2, via the corresponding 6-butyl-1,2-dihydro-2-oxo-1-[2'-(1(or 2)-triphenylmethyl-1H(or 2H)-tetrazol-5-yl)biphenyl-4-yl-methyl]pyridines:
3-pyrrolidino-
3-piperidino-
3-succinimido-
3-phthalimido-
3-benzamido-
3-tert-butoxycarbonylamino-
3-N'-butylureido-
3-N'-phenylureido-
3-N'-benzylureido-
3-N-methylbenzamido-
3-cyanomethyl-
3-ethoxycarbonylmethyl-
3-(tetrazol-5-ylmethyl)-
3-acetamidomethyl-, m.p. 183° (dec.)
3-butyramidomethyl-
3-phenylacetamidomethyl-
3-tert-butoxycarbonylaminomethyl-, m.p. 112°
3-phenoxycarbonylaminomethyl-
3-benzyloxycarbonylaminomethyl-
3-ureidomethyl-
3-N'-butylureidomethyl-, m.p. 275°
3-N'-cyclohexylureidomethyl-, m.p. 298°
3-N'-phenylureidomethyl-, m.p. 297°
3-N',N'-dimethylureidomethyl-
3-diethylaminomethyl-
3-diisopropylaminomethyl-
3-pyrrolidinomethyl-
3-piperidinomethyl-
3-(N-methylacetamidomethyl)-
3-(N-isopropylacetamidomethyl)-
3-(N-butyl-N'-methylureidomethyl)-
3-(N,N'-dimethylureidomethyl)-
3-(N,N',N'-trimethylureidomethyl)-
3-(N-butyl-N'-phenylureidomethyl)-
3-(N-benzyl-N'-methylureidomethyl)-
3-(N-butyl-N-isobutoxycarbonylaminomethyl)-
3-(N-isopropyl-N-benzyloxycarbonylaminomethyl)-.

6-Butyl-1-(2'-cyanobiphenyl-4-ylmethyl)-1,2-dihydro-2-oxo-3-(1H-tetrazol-5-ylmethyl)pyridine is obtained analogously from 6-butyl-1-(2'-cyanobiphenyl-4-ylmethyl)-1,2-dihydro-2-oxo-3-(1(or 2) -triphenylmethyl-1H(or 2H)-tetrazol-5-ylmethyl)pyridine.

EXAMPLE 4

A mixture of 1 g of 1-p-aminobenzyl-6-butyl-1,2-dihydro-2-oxopyridine, 0.6 g of phthalic anhydride and 40 ml of $CHCl_3$ is stirred for 16 hours at 20°. The phthalic acid mono-4-(6-butyl-1,2-dihydro-2-oxopyrid-1-ylmethyl)anilide which precipitates out is filtered off.

Preparation of the starting material:

(a) 3 g of IIIa are dissolved in 75 ml of methanol, and a solution of 0.4 g of Na in 10 ml of methanol is added dropwise at 20°, with stirring. The mixture is stirred for a further 45 min and evaporated, the residue is dissolved in 30 ml of DMF and cooled to 0°, a solution of 3.7 g of p-nitrobenzyl bromide is added at this temperature and the mixture is stirred for 16 hours at 20°. It is evaporated and worked up in conventional manner to give 6-butyl-1-p-nitrobenzyl-1,2-dihydro-2-oxo-pyridine.

(b) A solution of 1.7 g of 6-butyl-1-p-nitrobenzyl-1,2-dihydro-2-oxopyridine in 50 ml of methanol is hydrogenated on 1.7 g of Raney Ni at 20° until the uptake of $H_2$ has ceased. The mixture is filtered and evaporated to give 1-p-aminobenzyl-6-butyl-1,2-dihydro-2-oxopyridine.

EXAMPLE 5

A mixture of 2.56 g of 6-butyl-1-p-aminobenzyl-1,2-dihydro-2-oxopyridine, 3 ml of triethylamine, 0.5 g of 4-dimethylaminopyridine and 120 ml of $CH_2Cl_2$ is cooled to 5° and a solution of 2.88 g of o-trifluoromethanesulfonamidobenzoyl chloride in 20 ml of $CH_2Cl_2$ is added dropwise. The mixture is stirred for a further 16 hours at 20°, evaporated and worked up in conventional manner to give 6-butyl-1-[4-(o-trifluoromethanesulfonamidobenzamido)benzyl]-1,2-dihydro-2-oxopyridine.

EXAMPLE 6

A mixture of 2.85 g of 6-butyl-1-p-carboxybenzyl-1,2-dihydro-2-oxopyridine, 12 g of thionyl chloride and 35 ml of $CHCl_3$ is boiled for 6 hours and evaporated. The crude acid chloride obtained is freed from thionyl chloride residues by dissolution several times in toluene and evaporation, and is dissolved in 50 ml of THF. This solution is added dropwise to a solution of 1.7 g of anthranilic acid and 0.8 g of NaOH in 100 ml of water and the mixture is stirred for 24 hours and acidified to pH 5 with hydrochloric acid. 6-Butyl-1-[4-(2-carboxyanilinocarbonyl)benzyl]-1,2-dihydro-2-oxopyridine is obtained after conventional working-up.

Preparation of the starting materials:

(a) IIIa is reacted with p-bromomethylbenzonitrile analogously to Example 1 to give 6-butyl-1-p-cyanobenzyl-1,2-dihydro-2-oxopyridine after chromatography on silica gel (methyl tert-butyl ether/methanol).

(b) A mixture of 1 g of 6-butyl-1-p-cyanobenzyl-1,2-dihydro-2-oxopyridine, 0.7 g of KOH, 20 ml of ethanol and 5 ml of water is boiled for 24 hours, with stirring, evaporated, dissolved in water and acidified with hydrochloric acid. The 6-butyl-1-p-carboxybenzyl-1,2-dihydro-2-oxopyridine which precipitates out is filtered off and washed with water.

EXAMPLE 7

A mixture of 1.19 g of o-cyanophenol, 0.75 g of $K_2CO_3$ and 10 ml of DMF is stirred for 0.5 hour. A solution of 3.34 g of 1-p-bromomethylbenzyl-6-butyl-1,2-dihydro-2-oxopyridine (obtainable by reaction of IIIa with p-benzyloxymethylbenzyl bromide to give 1-benzyloxymethylbenzyl-6-butyl-1,2-dihydro-2-oxopyridine, hydrogenolysis to give the 3-p-hydroxymethylbenzyl compound, and reaction with $PBr_3$) in 20 ml of DMF is added dropwise and the mixture is heated at 90° for 8 hours and evaporated to give 6-butyl-1-(4-o-cyanophenoxymethylbenzyl)-1,2-dihydro-2-oxopyridine after conventional working-up.

EXAMPLE 8

A mixture of 2.57 g of 6-butyl-1-p-hydroxybenzyl-1,2-dihydro-2-oxopyridine (obtainable from IIIa and p-hydroxybenzyl bromide), 0.5 g of $CH_3ONa$ and 40 ml of DMSO is stirred for 0.5 hour. A solution of 2.2 g of o-cyanobenzyl bromide in 15 ml of DMSO is added dropwise and the mixture is stirred for 16 hours at 20° and evaporated to give 6-butyl-1-(4-o-cyanobenzyloxybenzyl)-1,2-dihydro-2-oxopyridine after conventional working-up.

EXAMPLE 9

A mixture of 404 mg of 6-butyl-1-[4-(2-methoxycarbonylanilinocarbonyl)benzyl]-1,2-dihydro-2-oxopyridine, 10 ml of 0.1N aqueous NaOH solution and 17 ml of THF is left to stand for 48 hours at 20°. The THF is evaporated off, the residue is acidified with HCl and extracted with methylene chloride and the extract is dried over $Na_2SO_4$ to give 6-butyl-1-[4-(2-carboxyanilinocarbonyl)benzyl]-1,2-dihydro-2-oxopyridine after evaporation.

The following are obtained analogously from the corresponding methyl or ethyl esters:

6-butyl-1,2-dihydro-2-oxo-1-(2'-cyanobiphenyl-4-ylmethyl)pyridine-3-carboxylic acid 6-butyl-1,2-dihydro-2-oxo-1-(2'-cyanobiphenyl-4-ylmethyl)pyridine-3-acetic acid 6-butyl-1-[2'-(tetrazol-5-yl)biphenyl-4-ylmethyl]-1,2-dihydro-2-oxopyridine-3-acetic acid.

EXAMPLE 10

A mixture of 400 mg of 6-butyl-3-cyanomethyl-1-(2'-methoxycarbonylbiphenyl-4-ylmethyl)-1,2-dihydro-2-oxopyridine and 2.2 ml of 1N aqueous KOH solution is boiled for 3 hours, cooled and acidified with hydrochloric acid. 6-Butyl-3-carbamoylmethyl-1-(2'-carboxybiphenyl-4-ylmethyl)-1,2-dihydro-2-oxopyridine is obtained after conventional working-up.

EXAMPLE 11

A mixture of 472 mg of 3-tert.-butoxycarbonylaminomethyl-6-butyl-1-(2'-cyanobiphenyl-4-ylmethyl)-1,2-dihydro-2-oxopyridine, 206 mg of trimethyltin azide and 12 ml of xylene is boiled for 96 hours; a further 0.2 g of azide is added after 48 hours. The mixture is cooled, treated with ethereal hydrochloric acid and evaporated. Chromatography of the residue (silica gel; methylene chloride/methanol 95:5) yields 3-tert.-butoxycarbonylaminomethyl-6-butyl-1,2-dihydro-2-oxo-1-[2'-(tetrazol-5-yl)-biphenyl-4-ylmethyl]pyridine; m.p. 105°. The corresponding K salt is prepared therefrom in conventional manner.

EXAMPLE 12

6-Butyl-1,2-dihydro-2-oxo-3-(tetrazol-5-yl)-1-[2'-(tetrazol-5-yl)biphenyl-4-ylmethyl]pyridine, m.p. 259° (dec.) Rf 0.1 (7:3), is obtained from 6-butyl-3-cyano-1-(2'-cyanobiphenyl-4-ylmethyl)-1,2-dihydro-2-oxopyridine analogously to Example 11, except that 2 equivalents of trimethyltin azide are used. Dipotassium salt, m.p. 235°.

6-Butyl-3-cyano-1,2-dihydro-2-oxo-1-[2'-(tetrazol-5-yl)biphenyl-4-ylmethyl]pyridine is obtained as a by-product (separable by chromatography).

6-Methyl-1,2-dihydro-2-oxo-5-propyl-3-(tetrazol-5-yl)-1-[2'-(tetrazol-5-yl)biphenyl-4-ylmethyl]pyridine can be prepared analogously from 3-cyano-1-(2'-cyanobiphenyl-4-ylmethyl)-6-methyl-1,2-dihydro-2-oxo-5-propylpyridine.

EXAMPLE 13

A mixture of 472 mg of 3-tert.-butoxy-carbonylaminomethyl-6-butyl-1-(2'-cyanobiphenyl-4-ylmethyl)-1,2-dihydro-2-oxopyridine, 700 mg of $NH_4Cl$, 700 mg of $NaN_3$ and 4 ml of DMF is stirred for 36 hours at 120°. It is cooled, the NaCl formed is filtered off and the filtrate is evaporated and worked up with aqueous hydrochloric acid/methylene chloride in conventional manner to give 6-butyl-1,2-dihydro-2-oxo-1-[2'-(tetrazol-5-yl)biphenyl-4-ylmethyl]pyridine, m.p. 105°.

EXAMPLE 14 a) A solution of 1 g of 6-butyl-1-(2'-nitrobiphenyl-4-ylmethyl)-1,2-dihydro-2-oxopyridine in 30 ml of ethanol is hydrogenated on 1 g of Raney Ni at 20° until the uptake of $H_2$ has ceased. The mixture is filtered and evaporated to give 1-(2'-aminobiphenyl-4-ylmethyl)-6-butyl-1,2-dihydro-2-oxopyridine.

b) A solution of 2.82 g of trifluoromethanesulfonic anhydride in 10 ml of $CH_2Cl_2$ is added dropwise to a solution of 3.32 g of 1-(2'-aminobiphenyl-4-ylmethyl)-6-butyl-1,2-dihydro-2-oxopyridine and 1.01 g of triethylamine in 30 ml of $CH_2Cl_2$ at −50° to −60°. The mixture is left to warm up to 20° and poured into dilute acetic acid to give 6-butyl-1-(2'-trifluoromethanesulfonamidobiphenyl-4-ylmethyl)-1,2-dihydro-2-oxopyridine after conventional working-up.

EXAMPLE 15

15 mg of $NaBH_4$ are added at 20° to a solution of 370 mg of 6-butyl-1-(2'-cyanobiphenyl-4-ylmethyl)-3-formyl-1,2-dihydro-2-oxopyridine in 5 ml of isopropanol, with stirring. After further stirring (1 hour), dilute hydrochloric acid is added dropwise until the evolution of $H_2$ has ceased, and the mixture is evaporated. 6-Butyl-1-

(2'-cyanobiphenyl-4-ylmethyl)-3-hydroxymethyl-1,2-dihydro-2-oxopyridine is obtained after conventional working-up.

EXAMPLE 16

0.07 ml of bromine is added dropwise at 0° to a solution of 280 mg of NaOH in 6 ml of water, with stirring. 360 mg of 6-butyl-3-carbamoyl-1-(2'-cyanobiphenyl-4-ylmethyl)-1,2-dihydro-2-oxopyridine are then added. The mixture is heated for 3 hours on a steam bath, acidified with 6N hydrochloric acid and stirred for a further 30 minutes. It is neutralized with 10% KHCO$_3$ solution, cooled and worked up in conventional manner to give 3-amino-6-butyl-1-(2'-cyanobiphenyl-4-ylmethyl)-1,2-dihydro-2-oxopyridine.

EXAMPLE 17

A solution of 1 g of 3-tert-butoxycarbonylamino-6-butyl-1-(2'-cyanobiphenyl-4-ylmethyl)-1,2-dihydro-2-oxopyridine in 20 ml of a 4N HCl solution in dioxane is stirred for 1 hour at 20° and then evaporated to give 3-amino-6-butyl-1-(2'-cyanobiphenyl-4-ylmethyl)-1,2-dihydro-2-oxopyridine in the form of the hydrochloride.

EXAMPLE 18

A suspension of 370 mg of 6-butyl-1-(2'-cyanobiphenyl-4-ylmethyl)-3-formyl-1,2-dihydro-2-oxopyridine, 770 mg of ammonium acetate, 61 mg of NaBH$_3$CN and 400 mg of a powdered 3 Å molecular sieve in 10 ml of isopropanol is stirred under argon for 3 days at 20°. It is filtered, the material on the filter is washed with methanol and the filtrate is evaporated. 3-Aminomethyl-6-butyl-1-(2'-cyanobiphenyl-4-ylmethyl)-1,2-dihydro-2-oxopyridine is obtained after conventional working-up (sodium hydroxide solution/methylene chloride), m.p. 118°.

3-Aminomethyl-6-butyl-1,2-dihydro-2-oxo-1-[2'-(tetrazol-5-yl)biphenyl-4-ylmethyl]pyridine is obtained analogously from 6-butyl-3-formyl-1,2-dihydro-2-oxo-1-[2'-(tetrazol-5-yl)biphenyl-4-ylmethyl]pyridine, decomposition starting at 75°.

EXAMPLE 19

A mixture of 3.7 g of 6-butyl-1-(2'-cyanobiphenyl-4-ylmethyl)-3-formyl-1,2-dihydro-2-oxopyridine, 0.59 g of isopropylamine and 3.55 g of titanium tetraisopropoxide is stirred for 2 hours at 20° under N$_2$. 10 ml of absolute ethanol and then 610 mg of NaBH$_3$CN are added, the mixture is stirred for a further 20 hours, 2 ml of water are then added and the mixture is filtered. The filtrate is evaporated. 6-Butyl-1-(2'-cyanobiphenyl-4-ylmethyl)-3-isopropylaminomethyl-1,2-dihydro-2-oxopyridine is obtained after conventional working-up.

The following are obtained analogously with butylamine or benzylamine:
6-butyl-3-butylaminomethyl-1-(2'-cyanobiphenyl-4-ylmethyl)-1,2-dihydro-2-oxopyridine
3-benzylaminomethyl-6-butyl-1-(2'-cyanobiphenyl-4-ylmethyl)-1,2-dihydro-2-oxopyridine, oil, Rf 0.15 (dichloromethane/methanol 95:5)
and the following are obtained from 6-butyl-3-formyl-1-[2'-(tetrazol-5-yl)biphenyl-4-ylmethyl]-1,2-dihydro-2-oxopyridine:
6-butyl-3-isopropylaminomethyl-1-[2'-(tetrazol-5-yl)biphenyl-4-ylmethyl]-1,2-dihydro-2-oxopyridine
6-butyl-3-butylaminomethyl-1-[2'-(tetrazol-5-yl)biphenyl-4-ylmethyl]-1,2-dihydro-2-oxopyridine
3-benzylaminomethyl-6-butyl-1-[2'-(tetrazol-5-yl)biphenyl-4-ylmethyl]-1,2-dihydro-2-oxopyridine.

EXAMPLE 20

6-Butyl-1-(2'-cyanobiphenyl-4-ylmethyl)-3-isopropylamino-1,2-dihydro-2-oxopyridine is obtained analogously to Example 19 from 3-amino-6-butyl-1-(2'-cyanobiphenyl-4-ylmethyl)-1,2-dihydro-2-oxopyridine and acetone/titanium tetraisopropoxide/NaBH$_3$CN.

The following are obtained analogously with butyraldehyde, benzaldehyde or hexafluoroacetone from the corresponding 3-amino or 3-aminomethyl compounds:
6-butyl-3-butylamino-1-(2'-cyanobiphenyl-4-ylmethyl)-1,2-dihydro-2-oxopyridine
3-benzylamino-6-butyl-1-(2'-cyanobiphenyl-4-ylmethyl)-1,2-dihydro-2-oxopyridine
6-butyl-3-(1,1,1,3,3,3-hexafluoro-2-propylamino)-1-(2'-cyanobiphenyl-4-ylmethyl)-1,2-dihydro-2-oxopyridine
6-butyl-3-(1,1,1,3,3,3-hexafluoro-2-propylaminomethyl)-1-(2'-cyanobiphenyl-4-ylmethyl)-1,2-dihydro-2-oxopyridine
3-benzylamino-6-butyl-1,2-dihydro-2-oxo-1-[2'-(tetrazol-5-yl)biphenyl-4-ylmethyl]pyridine
6-butyl-3-(1,1,1,3,3,3-hexafluoro-2-propylamino)-1,2-dihydro-2-oxo-1-[2'-(tetrazol-5-yl)biphenyl-4-ylmethyl]pyridine
6-butyl-3-(1,1,1,3,3,3-hexafluoro-2-propylaminomethyl)-1,2-dihydro-2-oxo-1-[2'-(tetrazol-5-yl)biphenyl-4-ylmethyl]pyridine.

EXAMPLE 21

Analogously to Example 1, there are obtained from IIa with 6-butyl-1,2-dihydro-3-methylsulfonylaminomethyl-, -3-trifluoromethylsulfonylaminomethyl-, -3-phenylsulfonylaminomethyl- or -3-p-tolylsulfonylaminomethyl-2-oxo-pyridine the following 6-butyl-1-(2'-cyanobiphenyl-4-yl)-methyl-1,2-dihydro-2-oxo-pyridines:
3-methylsulfonylaminomethyl-, m.p. 59°
3-trifluoromethylsulfonylaminomethyl-
3-phenylsulfonylaminomethyl-
3-p-tolylsulfonylaminomethyl-, m.p. 119°.

EXAMPLE 22

Analogously to Example 11, the following 6-butyl-1-[2'-(5-tetrazolyl)-biphenylyl-4-methyl]-1,2-dihydro-2-oxo-pyridines are obtained from the 2'cyano-biphenyl-4-yl compounds mentioned in Example 21 with trimethyltin azide:
3-methylsulfonylaminomethyl-
3-trifluoromethylsulfonylaminomethyl-
3-phenylsulfonylaminomethyl-
3-p-tolysulfonylaminomethyl-.

EXAMPLE 23

Analogously to Example 1, there are obtained from IIa the following 6-butyl-1-(2'-cyano-biphenyl-4-yl-methyl)-1,2-dihydro-2-oxo-pyridines:
with 3-N-benzyl-N-tert.-butoxycarbonyl-aminomethyl-6-butyl-1,2-dihydro-2-oxo-pyridine:
-3-N-benzyl-N-tert-butoxycarbonyl-aminomethyl-, Rf 0.35 (petroleum ether/methyl tert.-butyl ether 6:4);
with 6-butyl-3-N-methyl-N-p-toluenesulfonyl-aminomethyl-1,2-dihydro-2-oxo-pyridine:
-3-N-methyl-N-p-toluenesulfonyl-aminomethyl-, Rf 0.49 (petroleum ether/ethyl acetate 1:1):

with 3-N-acetyl-N-benzyl-aminomethyl-6-butyl-1,2-dihydro-2-oxo-pyridine:
-3-N-acetyl-N-benzyl-aminomethyl-, Rf 0.27 (ethyl acetate/petroleum ether 9:1);
with 6-butyl-3-N',N'-diphenylureidomethyl-1,2-dihydro-2-oxo-pyridine:
-3-N',N'-diphenylureidomethyl-, Rf 0.11 (petroleum ether/ethyl acetate 1:1);
with 6-butyl-3-N',N'-diethylureidomethyl-1,2-dihydro-2-oxopyridine: -3-N',N'-diethylureidomethyl-;
with 6-butyl-3-N',N'dimethylureidomethyl-1,2-dihydro-2-oxo-pyridine: -3-N',N'-dimethylureidomethyl-.

EXAMPLE 24

Analogously to Example 11, the following 6-butyl-1-[2'-(5-tetrazolyl)-biphenylyl-4-methyl]-1,2-dihydro-2-oxo-pyridines are obtained from the 2'-cyanobiphenylyl-4-methyl compounds mentioned in Example 23 with trimethyltin azide:

-3-N-benzyl-N-tert.-butoxycarbonyl-aminomethyl-, Rf 0.43 (dichloromethane/methanol 95:5);
-3-N-methyl-N-p-toluenesulfonyl-aminomethyl-, m.p. 110°;
-3-N-acetyl-N-benzyl-aminomethyl-, m.p. 132°; K salt, m.p. 196°;
-3-N',N'-diphenylureidomethyl-,Rf 0.37 (dichloromethane/methanol 9:1);
-3-N',N'-diethylureidomethyl-, Rf 0.28 (dichloromethane/methanol 9:1);
-3-N',N'-dimethylureidomethyl-, m.p. 113°; K salt, m.p. 271°.

The following Examples relate to pharmaceutical formulations containing active ingredients of formula I or their salts.

EXAMPLE A

Tablets and coated tablets

Tablets of the following composition are produced by pressing in conventional manner and, where necessary, are provided with a conventional sucrose-based coating:

| | |
|---|---|
| Active ingredient of formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

EXAMPLE B

Hard gelatin capsules

Conventional two-part hard gelatin capsules are each filled with

| | |
|---|---|
| Active ingredient of formula I | 100 mg |
| Lactose | 150 mg |
| Cellulose | 50 mg |
| Magnesium stearate | 6 mg |

EXAMPLE C

Soft gelatin capsules

Conventional soft gelatin capsules are filled with a mixture consisting in each case of 50 mg of active ingredient of formula I and 250 mg of olive oil.

EXAMPLE D

Ampoules

A solution of 200 g of active ingredient of formula I in 2 kg of propane-1,2-diol is made up to 10 l with water and filled into ampoules so that each ampoule contains 20 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1,2-dihydro-2-oxopyridine compound of formula I

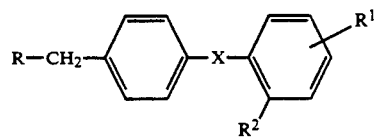

wherein
R is the radical

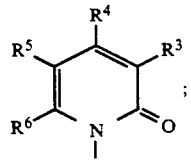

$R^1$ is H, Hal, A, OA or $NO_2$;
$R^2$ is COOH, COOA, CN, $NO_2$, $NH_2$, $NHCOR^7$, $NHSO_2R^7$ or tetrazol-5-yl;
$R^3$ is $CH_2NR^{10}R^{11}$, or tetrazol-5-yl;
$R^4$ is H or A;
$R^5$, $R^6$ and $R^{10}$ are in each case independently H, A, alkenyl having 2–6 C atoms, alkynyl having 2–6 C atoms, Ar or Ar-alkyl having 1–6 C atoms in the alkyl moiety;
$R^7$ is A or A monosubstituted or polysubstituted by F;
$R^{11}$ is H, A, A monosubstituted or polysubstituted by F, Ar, Ar-alkyl having 1–6 C atoms in the alkyl moiety, CO-A, CO-Ar, CO-alkyl-Ar having 1–6 C atoms in the alkyl moiety, COOA, COOAr, COO—alkyl—Ar having 1–6 C atoms in the alkyl moiety, $CONR^{12}R^{13}$, $SO_2R^7$ or $SO_2Ar$,
$NR^{10}R^{11}$ can also be pyrrolidino, piperidino, morpholino, succinimido or phthalimido;
$R^{12}$ and $R^{13}$ are in each case independently H, A, cycloalkyl having 3–8 C atoms, alkenyl having 2–6 C atoms, alkynyl having 2–6 C atoms, or Ar;
X is absent or is —CO—, —O—, —NH—CO—, —CO—NH—, —$CH_2$—O— or —O—$CH_2$—;
A is alkyl having 1–6 C atoms;
Ar is phenyl which is unsubstituted or monosubstituted by A, OA, $CF_3$, Hal or $NO_2$; and
Hal is F, Cl, Br or I; or
a physiologically acceptable salt.

2. A compound according to claim 1, wherein said compound is:
6-butyl-1,2-dihydro-2-oxo-3-(tetrazol-5-yl)-1-[2'-(tetrazol-5-yl)biphenyl-4-ylmethyl]pyridine or a physiologically acceptable salt thereof.

3. A compound according to claim 1, wherein $R^3$ is $CH_2NR^{10}R^{11}$.

4. A compound according to claim 1, wherein $R^3$ is tetrazol-5-yl.

5. A compound according to claim 1, wherein X is absent.

6. A compound according to claim 1, wherein X is —CO—.

7. A compound according to claim 1, wherein X is —O—.

8. A compound according to claim 1, wherein X is —NH—CO—.

9. A compound according to claim 1, wherein X is —CO—NH—.

10. A compound according to claim 1, wherein X is —CH₂—O—.

11. A compound according to claim 1, wherein X is —O—CH₂—.

12. A compound according to claim 1, wherein
$R^1$ is H,
$R^2$ is COOH, COOA, CN or tetrazol-5-yl,
$R^3$ is $CH_2NHCH_2C_6H_5$, $CH_2NACONHC_6H_5$ or tetrazol-5-yl,
$R^4$ and $R^5$ are each independently H or A,
$R^6$ is A, and
X is absent.

13. A compound according to claim 1, wherein
$R^1$, $R^4$ and $R^5$ are each H,
$R^2$ is CN or tetrazol-5-yl,
$R^3$ is, tetrazol-5-yl,
$R^6$ is alkyl having 3-5 C atoms, and
X is absent.

14. A compound according to claim 1, wherein $R^3$ is $CH_2NHR^{11}$.

15. A compound according to claim 14, wherein $R^3$ is $CH_2NHA$.

16. A compound according to claim 14, wherein $R^3$ is $CH_2NH$—alkyl—Ar.

17. A compound according to claim 14, wherein $R^3$ is $CH_2NA$—CO—NHAr.

18. A compound according to claim 14, wherein $R^{11}$ is benzyl, CO—A, CO—Ar, CO—$CH_2C_6H_5$, COOA, COOAr, COO$CH_2C_6H_5$, $CONH_2$, CONHA, CONH—cycloalkyl, $CONA_2$ or CONHAr.

19. A compound according to claim 1, wherein $R^3$ is $CH_2NR^{10}R^{11}$ and $R^{11}$ is $CONR^{12}R^{13}$, $SO_2R^7$ or $SO_2Ar$.

20. A compound according to claim 1, wherein $R^1$, $R^4$ and $R^5$ are each H, $R^2$ is CN or tetrazol-5-yl, $R^3$ is $CH_2NR^{10}R^{11}$, $R^6$ is A and X is absent.

21. A pharmaceutical composition comprising at least one compound according to claim 1 and a physiologically acceptable carrier.

22. A pharmaceutical composition according to claim 19, wherein said composition contains 50-500 mg of a compound according to claim 1.

23. A method for the treatment of prophylaxis of angiotensin II-dependent hypertension, angiotensin II-dependent aldosteronism and/or angiotensin II-dependent cardiac insufficiency, comprising administering a compound according to claim 1.

24. A method for treating angiotensin II-dependent hypertension, comprising administering a compound according to claim 1.

25. A method according to claim 24, wherein said compound is administered in an amount of 0.1-50 mg/kg of body weight.

* * * * *